(12) United States Patent
Lempp et al.

(10) Patent No.: US 11,841,368 B2
(45) Date of Patent: Dec. 12, 2023

(54) METHOD AND MEANS FOR THE RAPID DETECTION OF HDV INFECTIONS

(71) Applicant: UNIVERSITÄT HEIDELBERG, Heidelberg (DE)

(72) Inventors: Florian Lempp, San Francisco, CA (US); Stephan Urban, Neustadt (DE)

(73) Assignee: UNIVERSITÄT HEIDELBERG, Heidelberg (DE)

( * ) Notice: Subject to any disclaimer, the term of this patent is extended or adjusted under 35 U.S.C. 154(b) by 571 days.

(21) Appl. No.: 17/054,298

(22) PCT Filed: May 16, 2019

(86) PCT No.: PCT/EP2019/062668
§ 371 (c)(1),
(2) Date: Nov. 10, 2020

(87) PCT Pub. No.: WO2019/219840
PCT Pub. Date: Nov. 21, 2019

(65) Prior Publication Data
US 2021/0239701 A1    Aug. 5, 2021

(30) Foreign Application Priority Data

May 17, 2018  (EP) .................................. 18172895

(51) Int. Cl.
| | | |
|---|---|---|
| *C07K 14/005* | (2006.01) | |
| *C07K 14/08* | (2006.01) | |
| *C07K 14/02* | (2006.01) | |
| *C12Q 1/70* | (2006.01) | |
| *A61K 39/29* | (2006.01) | |
| *G01N 33/576* | (2006.01) | |

(52) U.S. Cl.
CPC ....... *G01N 33/5765* (2013.01); *C07K 14/005* (2013.01); *G01N 33/5761* (2013.01)

(58) Field of Classification Search
CPC ....... A61P 31/20; C07K 14/005; C07K 14/01; C07K 14/02; C12N 2760/10134
See application file for complete search history.

(56) References Cited

U.S. PATENT DOCUMENTS 7,785,773 B1   8/2010   Anderson et al.

FOREIGN PATENT DOCUMENTS

| EP | 0 251 575 A1 | 1/1988 |
| WO | 2014/186409 A1 | 11/2014 |
| WO | 2017/132332 A1 | 8/2017 |

OTHER PUBLICATIONS

GenBank Accession No. SCC98288.1, 2017: pdf p. 1.*
Vaillant, Andrew "Nucleic acid polymers: Broad spectrum antiviral activity, antiviral mechanisms and optimization for the treatment of hepatitis B and hepatitis D infection," Antiviral Research 133:32-40, Jul. 9, 2016.

\* cited by examiner

*Primary Examiner* — Barry A Chestnut
(74) *Attorney, Agent, or Firm* — SALIWANCHIK, LLOYD & EISENSCHENK

(57) ABSTRACT

The present invention relates to a polypeptide and a nucleic acid encoding the polypeptide for use in a method of detecting the presence of hepatitis D virus (HDV) and/or of diagnosing an HDV infection and/or of monitoring the treatment of an HDV infection. The present invention further relates to an in vitro method, an immunographic test device as well as a kit. In particular, the present invention relates to a point of care diagnostic for HDV infections.

20 Claims, 19 Drawing Sheets
Specification includes a Sequence Listing.

Figure 2A

```
  1 MSRSESKKNR GGREEILEQW VSGRKKLEDL ERDLRKVKKK IKKLEDENPW LGNIKGILGK
 61 KDKDGEGAPP AKRARTDQME VDSGPRKRPL RGGFTDKERQ DHRRRKALEN KKKQLSAGGK
121 NLSKEEEEL RRLTEEDERR ERRVAGPRVG GVNPLEGGPR GAPGGGFVPS MQGVPESPFT
181 RTGEGLDIRG NQGFPWDILF PADPPFSPQS CRPQHHHHHH HH
```

Figure 2B

```
  1  MSRSESKKNR  GGREEILEQW  VSGRKKLEDL  ERDLRKVKKK  IKKLEDENPW  LGNIKGILGK
 61  KDKDGEGAPP  AKRARTDQME  VDSGPRKRPL  RGGFTDKERQ  DHRRRKALEN  KKKQLSAGGK
121  NLSKEEEEL   RRLTEEDERR  ERRVAGPRVG  GVNPLEGGPR  GAPGGGFVPS  MQGVPESPFT
181  RTGEGLDIRG  NQGFPWDILF  PADPPFSPQS  CRPQHHHHHH  HH
```

L-HDAg-consensus-His:

25 kDa
pI=9.9

```
  1 MSRSESKKNR GGREEILEQW VSGRKKLEDL ERDLRKVKKK IKKLEDENPW LGNIKGILGK
 61 KDKDGEGAPP AKRARTDQME VDSGPRKRPL RGGFTDKERQ DHRRRKALEN KKKQLSAGGK
121 NLSKEEEEL RRLTEEDERR ERRVAGPRVG GVNPLEGGPR GAPGGGFVPS MQGVPESPFT
181 RTGEGLDIRG NQGFPWDILF PADPPFSPQS CRPQHHHHHH HH
```

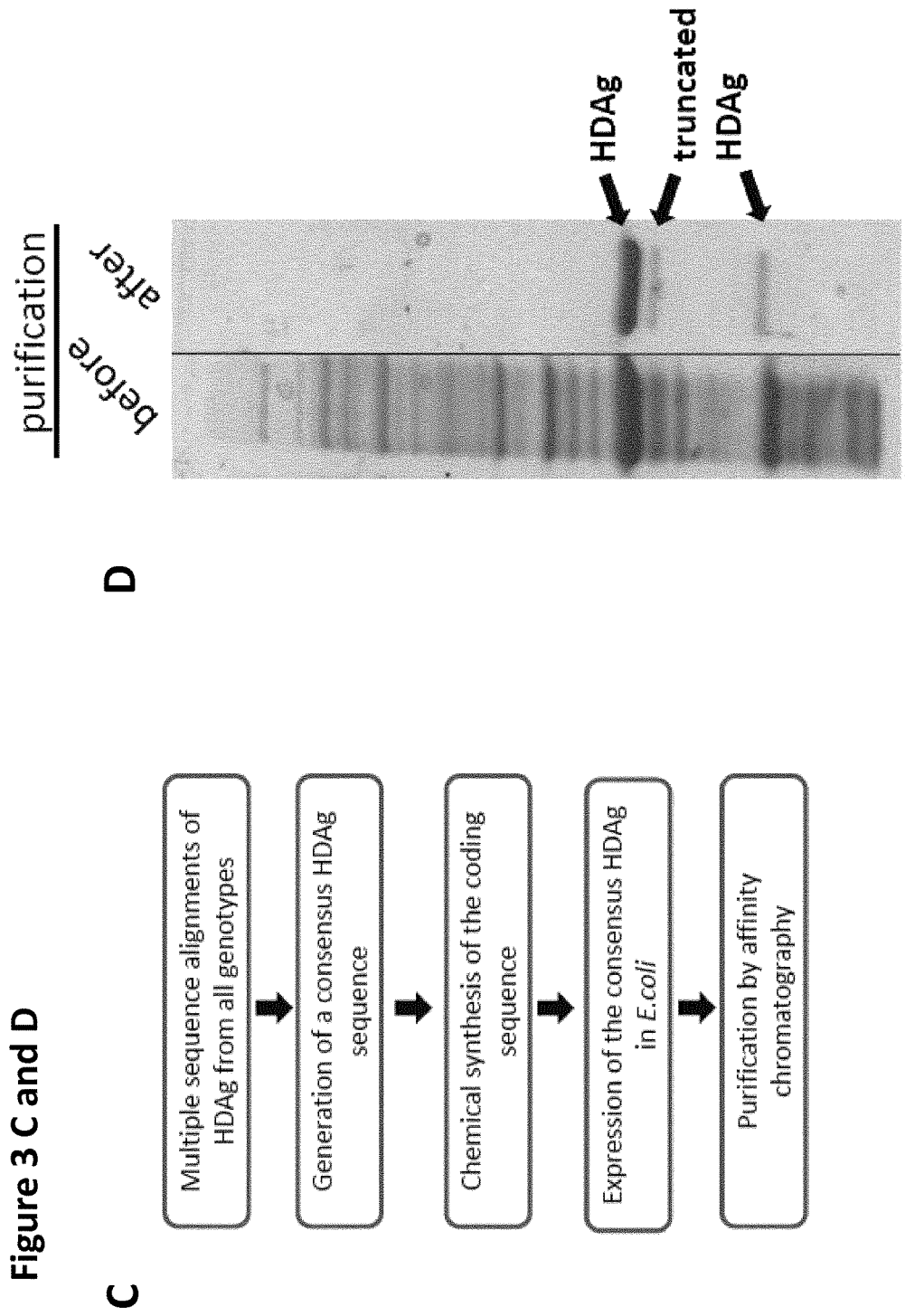
Figure 3 C and D

Figure 11 A and B
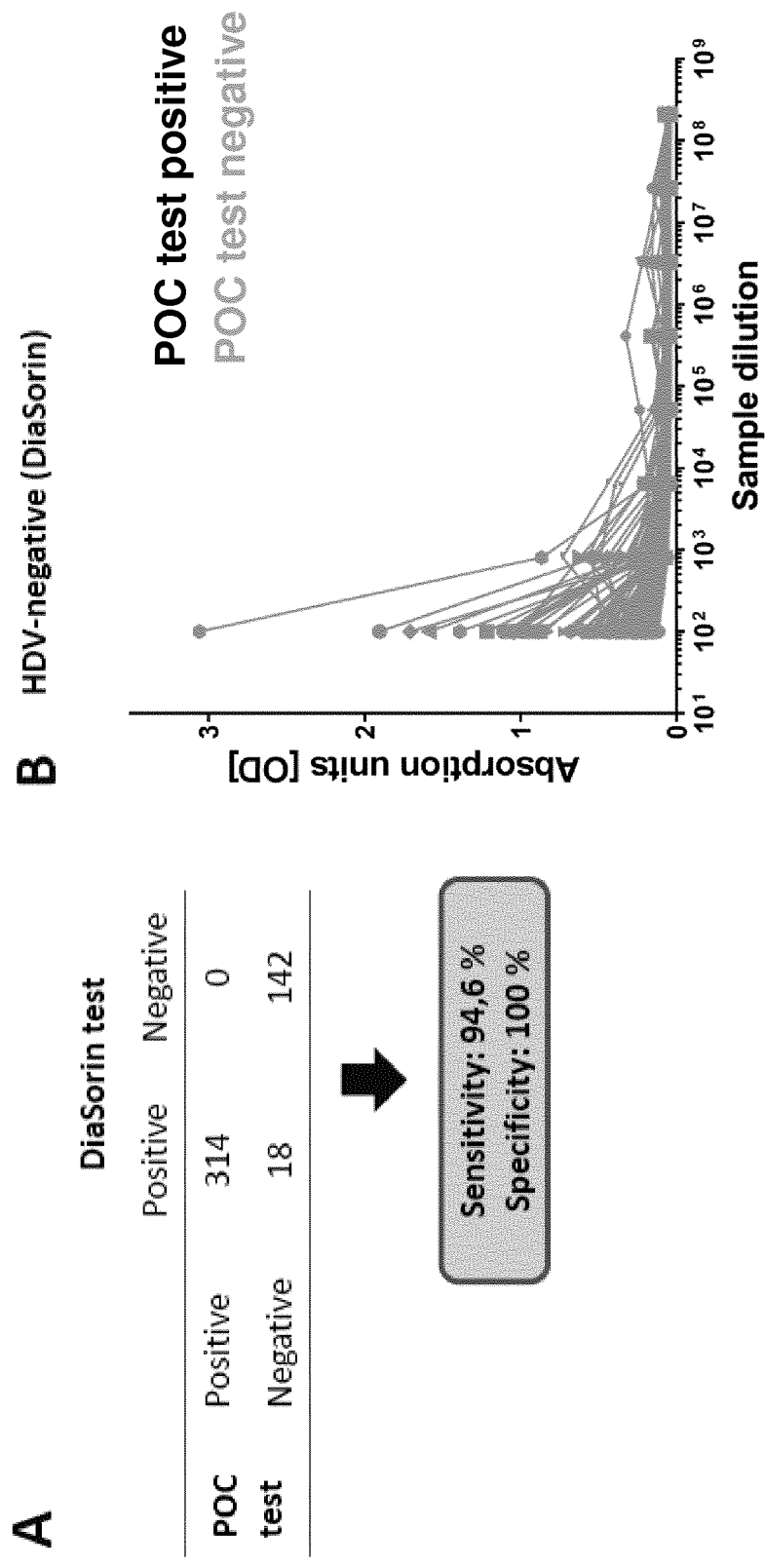

Figure 11 C and D
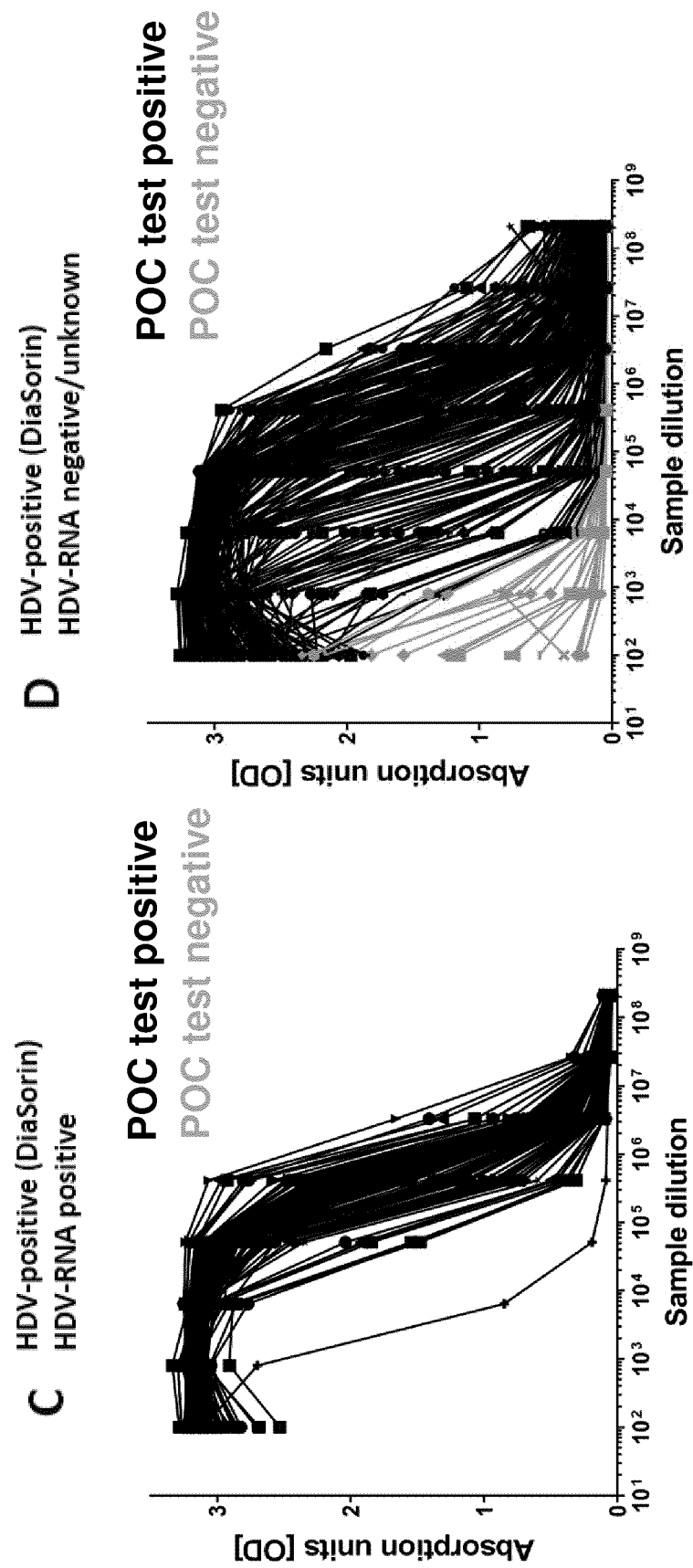

US 11,841,368 B2

METHOD AND MEANS FOR THE RAPID DETECTION OF HDV INFECTIONS

CROSS REFERENCE TO RELATED APPLICATIONS

This application is a National Stage Application of International Application Number PCT/EP2019/062668, filed May 16, 2019; which claims priority to European Application No. 18172895.7, filed May 17, 2018.

The Sequence Listing for this application is labeled "SeqList-09Nov20-ST25.txt", which was created on Nov. 9, 2020 and is 5 KB. The entire content is incorporated herein by reference in its entirety.

The present invention relates to a polypeptide and a nucleic acid encoding the polypeptide for use in a method of detecting the presence of hepatitis D virus (HDV) and/or of diagnosing an HDV infection and/or of monitoring the treatment of an HDV infection. The present invention further relates to an in vitro method, an immunographic test device as well as a kit.

In particular, the present invention relates to a point of care diagnostic for HDV infections.

BACKGROUND OF THE INVENTION

Chronic Hepatitis Delta Virus (HDV) infections represent the most severe form of viral hepatitis leading to cirrhosis and hepatocellular carcinoma. HDV is a satellite virus of Hepatitis B Virus (HBV), which means that all patients chronically infected with HDV are always co-infected with HBV. Worldwide, 250 million individuals are chronically infected with HBV, out of which ca. 20 million are co-infected with HDV.

According to guidelines, every HBV-infected individual should be tested for an HDV co-infection, as HDV co-infection significantly worsens the disease outcome and alters treatment regimens. In practice, however, latest studies show that only 8% (USA), 35% (Greece) or 40% (UK) of HBV-positive patients are tested for an HDV co-infection (Lempp and Urban, 2017). Reasons for the testing reluctance are: (1) laborious, time-intense and expensive diagnostic tests, (2) unawareness of medical doctors for HDV infections, (3) lacking of therapeutic options for HDV-infected individuals.

Reasons (2) & (3) will vanish in the near future as research funding agencies, pharmaceutical companies and federal institutions like FDA and EMA have recognized the need for a better treatment of HBV and HDV chronic infections and new treatment options are arising.

Three novel drugs are currently investigated in phase II trials in chronically HDV-infected patients. First, Lonafarnib, an orally administered prenylation inhibitor preventing the egress of enveloped HDV particles (Koh et al., 2015; Yurdaydin et al., 2015; Koh et al., 2014). Second, nucleic acid polymers like REP2139-Ca, which are administered intravenously and have been described to affect the HBsAg but presumably exhibits additional modes of action (Bazinet et al., 2015; Poutay et al., 2015; Bazinet et al., 2015-2; Vaillant et al., 2016). And third, Myrcludex B (Bulevirtide), a subcutaneously delivered myristoylated L-HBsAg-derived 47-mer lipopetide, which was developed by the present inventors and which irreversibly blocks the NTCP receptor of HDV (and HBV) thereby preventing de novo formation of HDV RNA- and cccDNA in naïve and regenerating hepatocytes (Bogomolov et al., 2016; Blank et al., 2016; Urban et al., 2014). All three drugs are being evaluated alone or in combination with pegIFNα and/or a nucleot(s)ide analogues like tenofovir. Responding to the urgent medical need of novel drugs for chronic Hepatitis D, Lonafarnib and Myrcludex B received orphan drug status by the European Medicines Agency (EMA) and the U.S. Food and Drug Administration (FDA). Lonafarnib received "Fast Track Status" by the FDA in 2015. Myrcludex B received "prime eligibility status" by the EMA in May 2017.

With a reasonable hope that one or more of these still experimental therapies will be approved in the near future a medical need for fast and convenient testing for HDV infection will arise.

SUMMARY OF THE INVENTION

According to the present invention this object is solved by providing a polypeptide comprising or consisting of an amino acid sequence of SEQ ID NO. 1 or SEQ ID NO. 2.

According to the present invention this object is solved by providing a polypeptide comprising or consisting of an amino acid sequence comprising or consisting of amino acid residues 1 to 195 of SEQ ID NO. 1 or 2.

According to the present invention this object is solved by providing a polypeptide comprising or consisting of an amino acid sequence comprising or consisting of amino acid residues 60 to 214 of SEQ ID NO. 1 or 2.

According to the present invention this object is solved by providing a polypeptide comprising or consisting of an amino acid sequence having at least 90% sequence identity to SEQ ID NO. 1.

According to the present invention this object is solved by providing a nucleic acid encoding a polypeptide of the present invention.

According to the present invention this object is solved by providing the polypeptide of the present invention or the nucleic acid of the present invention for use in a method of detecting the presence of hepatitis D virus (HDV) and/or of diagnosing an HDV infection and/or of monitoring the treatment of an HDV infection.

According to the present invention this object is solved by an in vitro method for detecting the presence of hepatitis D virus (HDV) and/or for diagnosing an HDV infection and/or for monitoring the treatment of an HDV infection in a sample of a subject, said method comprising
  providing the polypeptide of the present invention; and
  detecting for antibodies against the Hepatitis Delta Antigen (HDAg) in said sample.

According to the present invention this object is solved by an immunographic device for in vitro detecting the presence of Hepatitis D virus (HDV) in a sample of a subject, diagnosing an HDV infection and/or monitoring the treatment of an HDV infection, said device comprising a solid carrier coated with an anti-HDV IgG antibody binding agent, wherein the anti-HDV IgG antibody binding agent is the polypeptide of the present invention.

According to the present invention this object is solved by a kit for in vitro detecting the presence of Hepatitis D virus (HDV) in a sample of a subject, diagnosing an HDV infection and/or monitoring the treatment of an HDV infection, wherein the kit comprises:
  a) an immunographic device according to the present invention; and
  b) instructions for using the immunographic device to detect the presence of the said anti-HDV IgG antibodies in the sample.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "1 to 21" should be interpreted to include not only the explicitly recited values of 1 to 21, but also include individual values and sub-ranges within the indicated range. Thus, included in this numerical range are individual values such as 1, 2, 3, 4, 5 . . . . 17, 18, 19, 20, 21 and sub-ranges such as from 2 to 10, 8 to 15, etc. This same principle applies to ranges reciting only one numerical value, such as "at least 90%". Furthermore, such an interpretation should apply regardless of the breadth of the range or the characteristics being described.

Consensus Sequence of HDAg

As outlined above, the present invention provides a synthetic consensus sequence of Hepatitis Delta Antigen (HDAg).

The present invention provides a polypeptide comprising or consisting of an amino acid sequence of SEQ ID NO. 1 or SEQ ID NO. 2.

SEQ ID NO. 1 Synthetic HDAg Sequence (Consensus), 214 amino acids

```
  1 MSRSESKKNR GGREEILEQW VSGRKKLEDL ERDLRKVKKK IKKLEDENPW LGNIKGILGK

61 KDKDGEGAPP AKRARTDQME VDSGPRKRPL RGGFTDKERQ DHRRRKALEN KKKQLSAGGK

121 NLSKEEEEEL RRLTEEDERR ERRVAGPRVG GVNPLEGGPR GAPGGGFVPS MQGVPESPFT

181 RTGEGLDIRG NQGFPWDILF PADPPFSPQS CRPQ
```

SEQ ID NO. 2 Synthetic HDAg Sequence (Consensus) with a His-tag for recombinant expression, 222 amino acids

```
  1 MSRSESKKNR GGREEILEQW VSGRKKLEDL ERDLRKVKKK IKKLEDENPW LGNIKGILGK

61 KDKDGEGAPP AKRARTDQME VDSGPRKRPL RGGFTDKERQ DHRRRKALEN KKKQLSAGGK

121 NLSKEEEEEL RRLTEEDERR ERRVAGPRVG GVNPLEGGPR GAPGGGFVPS MQGVPESPFT

181 RTGEGLDIRG NQGFPWDILF PADPPFSPQS CRPQHHHHHH HH
```

The present invention provides a polypeptide comprising or consisting of an amino acid sequence having at least 90% sequence identity to SEQ ID NO. 1.

A polypeptide of the present invention also comprises polypeptides comprising or consisting of an amino acid sequence of SEQ ID NO. 1 (or SEQ ID NO. 2) having differences in one, two, three, four, five, six, seven, eight, nine, ten, 11, 12, 13, 14 and up to 21 amino acid positions.

For example, a polypeptide with different amino acids in two positions of the amino acid sequence of SEQ ID NO. 1 refers to a polypeptide consisting of an amino acid sequence having 99% sequence identity to SEQ ID NO. 1.

For example, a polypeptide with different amino acids in eleven positions of the amino acid sequence of SEQ ID NO. 1 refers to a polypeptide consisting of an amino acid sequence having 95% sequence identity to SEQ ID NO. 1.

For example, a polypeptide with different amino acids in 21 positions of the amino acid sequence of SEQ ID NO. 1 refers to a polypeptide consisting of an amino acid sequence having 90% sequence identity to SEQ ID NO. 1.

The present invention provides a polypeptide comprising or consisting of an amino acid sequence having at least 90% sequence identity to SEQ ID NO. 1.

The present invention provides a polypeptide comprising or consisting of an amino acid sequence comprising or consisting of amino acid residues 1 to 195 of SEQ ID NO. 1 or 2.

The present invention provides a polypeptide comprising or consisting of an amino acid sequence comprising or consisting of amino acid residues 60 to 214 of SEQ ID NO. 1 or 2.

As outlined above, the present invention provides a polypeptide comprising or consisting of an amino acid sequence selected from an amino acid sequence of SEQ ID NO. 1 or SEQ ID NO. 2, an amino acid sequence comprising or consisting of amino acid residues 1 to 195 of SEQ ID NO. 1 or 2, an amino acid sequence comprising amino acids comprising or consisting of amino acid residues 60 to 214 of SEQ ID NO. 1 or 2, or an amino acid sequence having at least 90% sequence identity to SEQ ID NO. 1.

As outlined above, the present invention provides a nucleic acid encoding a polypeptide of the present invention.

The present inventors have designed an in silico synthetic consensus sequence of all HDV genotypes.

Eight genotypes of HDV (HDV-1 to HDV-8) have been described so far, with <20% divergence within one genotype and up to 35% divergence between the different genotypes. The different genotypes show distinct geographical distributions: genotype 1 is prevalent worldwide, genotype 2 is mostly present in Asia, genotype 3 can exclusively be found in the Amazonas region in South America, genotype 4 was found in Taiwan and genotypes 5-8 are predominant in West and Central Africa.

It is absolutely required that a novel diagnostic is able to reliably detect HDV infections with all 8 genotypes, which is why this invention describes a synthetic sequence of the L-HDAg that includes all 8 genotypes.

The HDAg of the invention is pan-genotypic.

Medical Uses

As outlined above, the present invention provides the polypeptide of the present invention or the nucleic acid of the present invention for use in a method of detecting the presence of hepatitis D virus (HDV) and/or of diagnosing an HDV infection and/or of monitoring the treatment of an HDV infection.

In a preferred embodiment, antibodies against the Hepatitis Delta Antigen (HDAg) are detected in a sample of a subject.

Said anti-HDAg antibodies are IgG antibodies.

Preferably, the sample is serum, plasma, whole blood or saliva.

Preferably, the polypeptide or nucleic acid are used in an immunographic test device, such as a lateral flow assay (LFA) device, which is preferably a point-of-care device.

Preferably, HDV and HDV infections of all genotypes can be detected.

In one embodiment, further infections are detected, such as HBV infection.

Detection Method

As outlined above, the present invention provides an in vitro method for detecting the presence of hepatitis D virus (HDV) and/or for diagnosing an HDV infection and/or for monitoring the treatment of an HDV infection in a sample of a subject.

The method of the present invention is based on detecting the presence of antibodies against HDV.

Said Method Comprises
providing the polypeptide of the present invention; and
detecting for antibodies against the Hepatitis Delta Antigen (HDAg) in said sample.

Said method is preferably a point-of-care method or point-of-care testing.

"Point-of-care testing" (POCT), as used herein, refers to a medical diagnostic testing at or near the point of care, that is, at the time and place of patient care.

Point-of-care tests are simple medical tests that can, for example, be performed at the bedside. The driving notion behind POCT is to bring the test conveniently and immediately to the patient. This increases the likelihood that the patient, physician, and care team will receive the results quicker, which allows for better immediate clinical management decisions to be made. Point-of-care tests and methods are known in the art. For example, rapid diagnostic tests such as malaria antigen detection tests.

The driving notion behind POCT is to bring the test conveniently and immediately to the patient. This increases the likelihood that the patient, physician, and care team will receive the results quicker, which allows for better immediate clinical management decisions to be made. POCT is often accomplished through the use of transportable, portable, and handheld instruments and test kits. The goal is to collect the specimen and obtain the results in a very short period of time at or near the location of the patient so that the treatment plan can be adjusted as necessary before the patient leaves.

Many point-of-care test systems are realized as easy-to-use membrane-based test strips, often enclosed by a plastic test cassette. This concept often is realized in test systems for detecting pathogens.

Preferably, the sample is serum, plasma, whole blood or saliva.

Preferably, HDV and HDV infections of all genotypes can be detected.

In one embodiment, further infections are detected, such as HBV infection.

Test Device and Kit

As outlined above, the present invention provides an immunographic device.

Said immunographic device is for in vitro detecting the presence of Hepatitis D virus (HDV) in a sample of a subject, diagnosing an HDV infection and/or monitoring the treatment of an HDV infection.

Said immunographic device comprises a solid carrier coated with an anti-HDV IgG antibody binding agent.

Preferably, the anti-HDV IgG antibody binding agent is the polypeptide of the present invention.

In a preferred embodiment, the immunographic device comprises a porous membrane operably connected to
(a) a sample portion/pad,
(b) a conjugate portion/pad,
(c) a test portion/line comprising said anti-HDV IgG antibody binding agent,
(d) a control portion/line; and
(e) an absorbent portion/pad.

Preferably, the immunographic device is a lateral flow assay (LFA) device, which is more preferably a point-of-care device.

Lateral flow assays and respective devices are known in the art. LFAs can also be called a lateral flow immunoassay test, also known as the immunochromatography assay, or strip test. Lateral flow immunoassays are essentially immunoassays adapted to operate along a single axis to suit the test strip format. A typical lateral flow rapid test strip consist of the following components:

Sample pad—an adsorbent pad onto which the test sample is applied.

Conjugate or reagent pad—this contains antibodies specific to the target analyte conjugated to coloured particles (usually colloidal gold nanoparticles, or latex microspheres).

Reaction membrane—typically a nitrocellulose or cellulose acetate membrane onto which analyte-binding agents (such as anti-target analyte antibodies) are immobilized in a line that crosses the membrane to act as a capture zone or test line (a control zone will also be present, containing antibodies specific for the conjugate antibodies).

Wick or waste reservoir—a further absorbent pad designed to draw the sample across the reaction membrane by capillary action and collect it.

The components of the strip are usually fixed to an inert backing material and may be presented in a simple dipstick format or within a plastic casing with a sample port and reaction window showing the capture and control zones.

Preferably, the sample is serum, plasma, whole blood or saliva.

Preferably, HDV and HDV infections of all genotypes can be detected.

In one embodiment, further infections are detected, such as HBV infection.

In one embodiment, the conjugate portion/pad comprises a detection marker, which is preferably a colloidal metal, such as gold, or latex beads.

In one embodiment, the detection marker is directly or indirectly bound to an antibody, such as an anti-human antibody, or to an antibody-binding protein, such as Protein A or Protein G.

In one embodiment, the control portion/line comprises a binding agent to the detection marker or the moiety carrying the detection marker.

As outlined above, the present invention provides a kit for in vitro detecting the presence of Hepatitis D virus (HDV) in a sample of a subject, diagnosing an HDV infection and/or monitoring the treatment of an HDV infection.

Said kit comprises:
  a) an immunographic device according to the present invention; and
  b) instructions for using the immunographic device to detect the presence of said anti-HDV IgG antibodies in the sample.

Preferably, the sample is serum, plasma, whole blood or saliva.

Preferably, HDV and HDV infections of all genotypes can be detected.

In one embodiment, further infections are detected, such as HBV infection.

PREFERRED EMBODIMENTS

The human Hepatitis Delta Virus (HDV) is unique among all viral pathogens. Encoding only one protein (Hepatitis Delta Antigen; HDAg) within its viroid-like self-complementary RNA, HDV constitutes the smallest known virus in the animal kingdom. To disseminate in its host, HDV depends on a helper virus, the human Hepatitis B virus (HBV), which provides the envelope proteins required for HDV assembly (see FIG. 1). HDV affects an estimated 15 to 20 million out of the 240 million chronic HBV-carriers and disperses unequally in disparate geographical regions of the world. The disease it causes (chronic Hepatitis D) presents as the most severe form of viral hepatitis, leading to accelerated progression of liver dysfunction including cirrhosis and hepatocellular carcinoma and a high mortality rate. The lack of approved drugs interfering with specific steps of HDV replication poses a high burden for gaining insights into the molecular biology of the virus and, consequently, the development of specific novel medications that resiliently control HDV replication or, in the best case, functionally cure HDV infection or HBV/HDV co-infection.

The present invention discloses a solution for reason (1) for testing reluctance, as discussed herein, namely the so far available laborious, time-intense and expensive diagnostic tests. The primary diagnosis of HDV infection is performed by the detection of antibodies against the Hepatitis Delta Antigen (HDAg) in the serum of infected patients. This detection of HDAg-specific antibodies is currently performed by manual ELISA assays (offered by only very few companies worldwide). The assay is time-consuming (~4 hours per assay), requires a full laboratory equipment (e.g. absorption plate reader) and trained staff. Therefore, diagnosis can only be performed in a central laboratory of a large institution but not in a point-of-care setting.

Our invention describes a rapid point-of-care test device to detect antibodies against HDAg in the serum or even whole blood of patients. The test is based on the lateral flow assay (LFA) technique that is most widely known from pregnancy tests (see FIG. 4).

To specifically detect antibodies against HDAg, our invention uses recombinantly expressed HDAg protein that is based on an artificial consensus sequence of all HDV genotypes. There are 8 different HDV genotypes worldwide with different geographic distributions. By using this synthetic consensus construct, our LFA is able to detect HDV infections of all genotypes and can therefore be employed worldwide. Alternatively we can immobilize specific peptides that have been identified as the major antigenic epitopes.

The key advantages of our invention compared to the current diagnostics for HDV infection are:
  (1) Fast assay: less than 30 min assay time compared to 4 h with the manual ELISA.
  (2) Easy to use. No need for laboratory equipment or laboratory-trained staff. You only need to apply several drops of serum or whole blood to the test strip and wait for 5-10 min. Due to this, our LFA assay can be employed in a doctor's practice ("niedergelassener Arzt") or even for field studies in remote areas.
  (3) Low costs for production: while the conventional manual ELISA costs about 7€ per test, common manufacturing prices are about 1 € per test strip of the LFA.
  (4) Specific for all genotypes: the synthetic HDAg construct is designed as a consensus sequence of all genotypes and therefore, the test allows diagnosing infections of all genotypes. The HDAg of the invention is pan-genotypic.
  (5) A collection of serum samples from all genotypes was established and the assay was validated.
  The assay has a high sensitivity (94.6%) and high specificity (100%).
  (6) Combination of the anti-HDAg test with a test for HBV HBsAg to co-detect HBV and HDV infection on the same LFA strip (as multiplex strip).

The POC anti-HDV test of this invention allows easy and reliable diagnosis of HDV infection in hospitals and doctor's practices but also in remote areas or epidemiological field studies.

The following examples and drawings illustrate the present invention without, however, limiting the same thereto.

The RNA genome of HDV is packaged as a ribonucleoprotein together with the Hepatitis Delta Antigen (HDAg). Both virions share the same envelope proteins, the S-, M- and L-HBsAg. L-HBsAg is composed of S-HBsAg with two N-terminal elongations: preS2 and the N-terminally myristoylated preS1. From Lempp and Urban, 2017.

FIG. 2. Design of the L-HDAg Consensus Sequence.

2A-2B show a multiple sequence alignment of L-HDAg from several isolates of all eight HDV genotypes was computed using VectorNTI software and sequencing data provided in the NCBI database. The consensus sequence was determined from the multiple sequence alignment.

Figure 1:
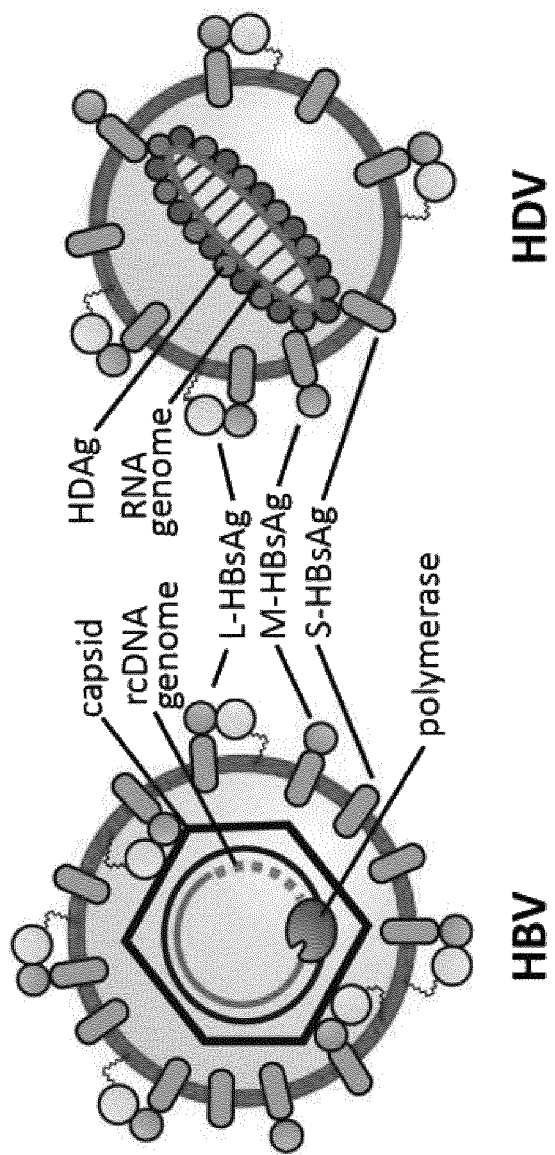
FIG. 1. Schematic Representation of HBV and HDV Virions.
Figure 3:
Figure 3:
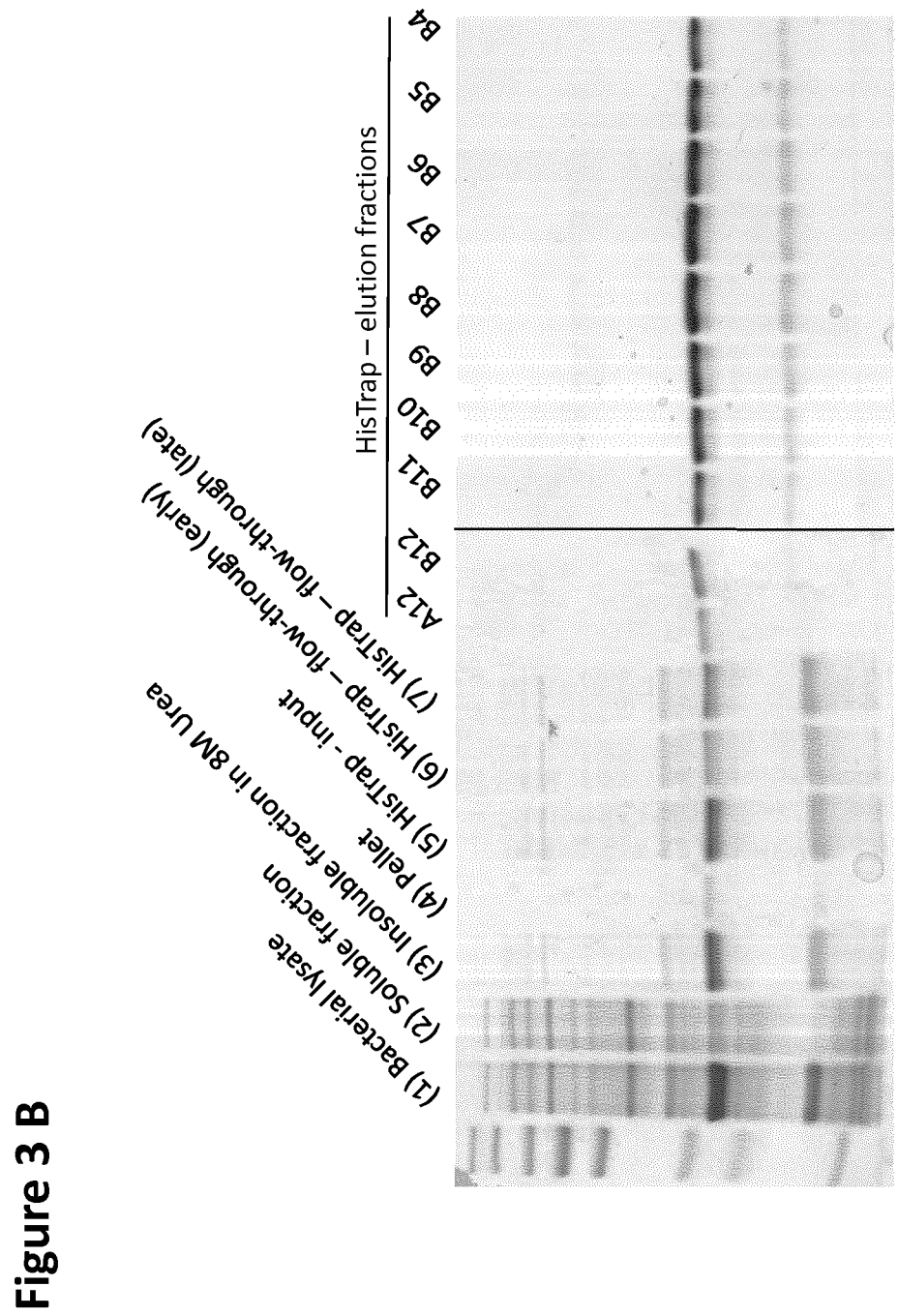
Figure 3:
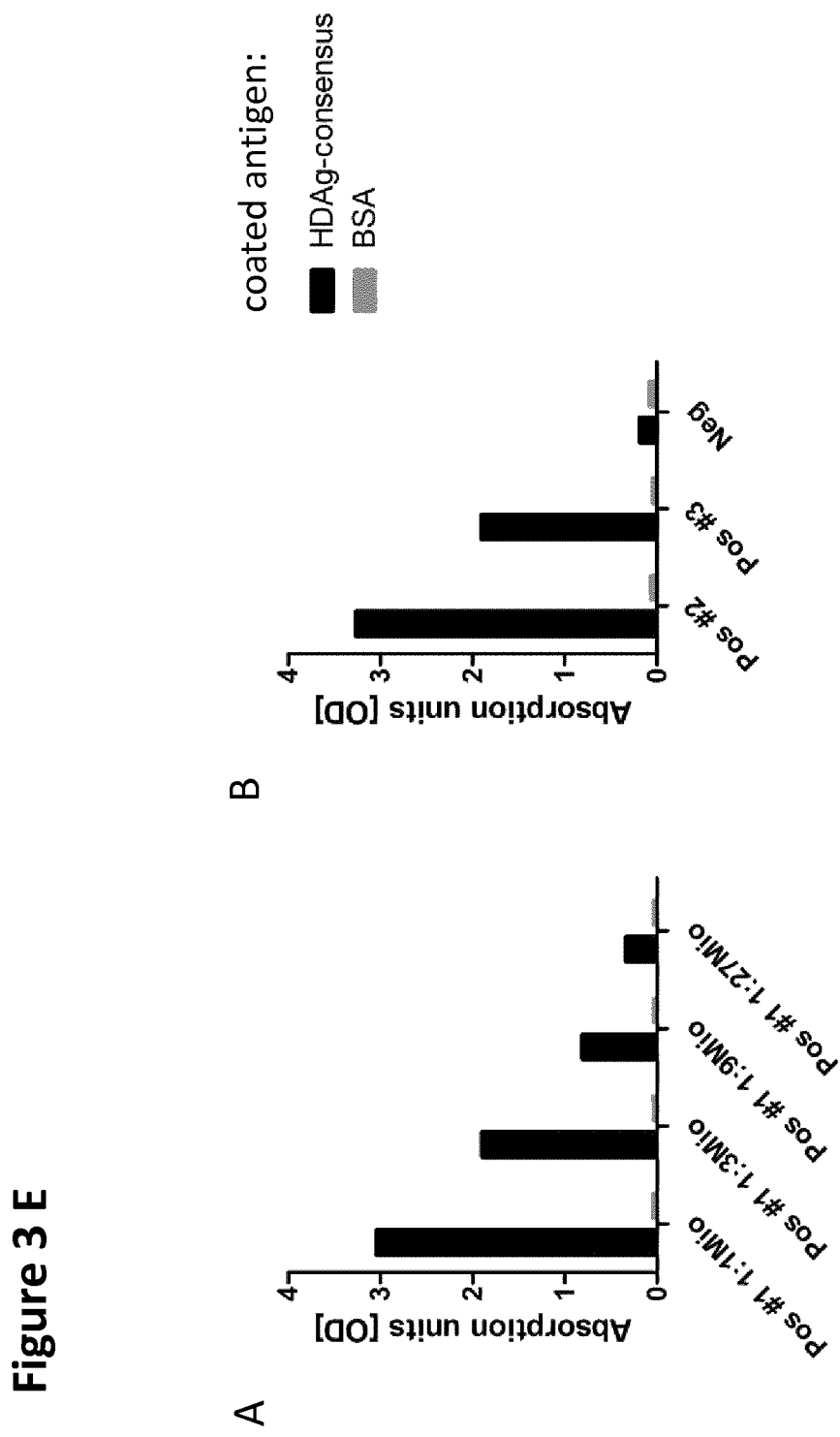

FIG. 3. Construct Design for a Recombinant HDAg.

A, Construct design for the bacterial expression of a recombinant HDAg. The Histidine-tag is fused C-terminally to the protein. Shown is also the consensus sequence.

B, Analysis of bacterial expression and purification of the construct by SDS-PAGE.

Protein was expressed in *E. coli* (1). Bacteria were lysed by a microfluidizer method. Lysate was ultracentrifuged and the inclusion bodies containing the recombinant L-HDAg were resolubilized in 8M Urea (3). Protein was purified by nickel-affinity chromatography and eluted using a linear gradient of imidazole.

C, Summary showing the development of the recombinant pan-genotypic HDAg.

D, Coomassie stained SDS-gel samples before (left) and after (right) purification. All three protein bands after purification represent HDAg as determined by mass spectrometry.

E, Antigenicity testing in ELISA.

Purified L-HDAg or bovine serum albumin (BSA) was coated on ELISA plates and incubated with (A) a serum of an HBV/HDV co-infected patient in increasing dilutions starting from 1:1.000.000 or (B) two sera of HBV/HDV co-infected patients or the serum of a healthy patient (neg), all at 1:2.000 dilution. After washing, the plates were incubated with an HRP-labeled anti-human secondary antibody and the enzymatic reaction was started by incubation with TMB substrate. All positive patient sera highly reacted with the coated L-HDAg but not with the BSA, while the serum of the negative patient did not react with both antigens. Note, that the pos #3 serum is derived from an HBV/HDV-coinfected patient with negative HDV viremia that therefore shows a lower amount of anti-HDV antibodies but is still highly reactive to the L-HDAg.

Figure 4:
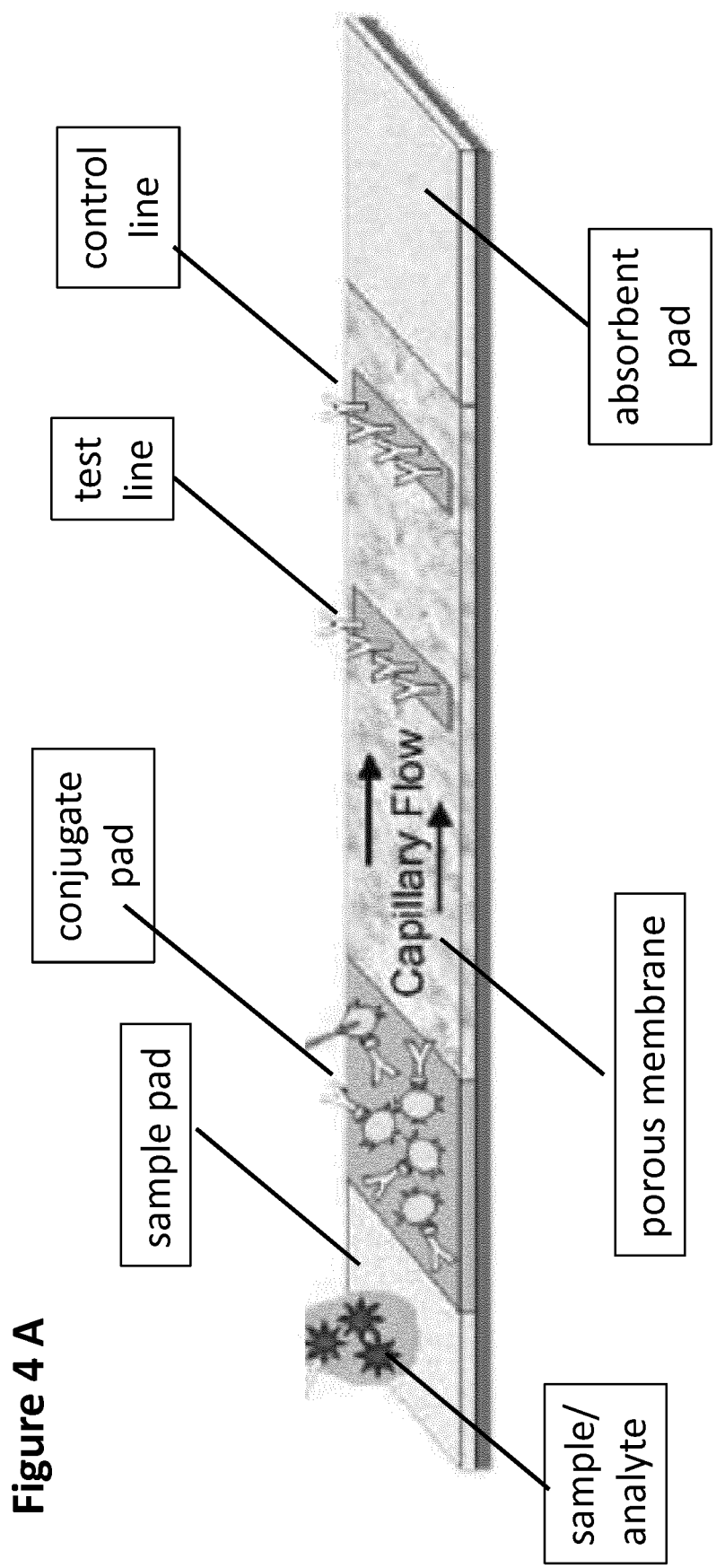
Figure 4:
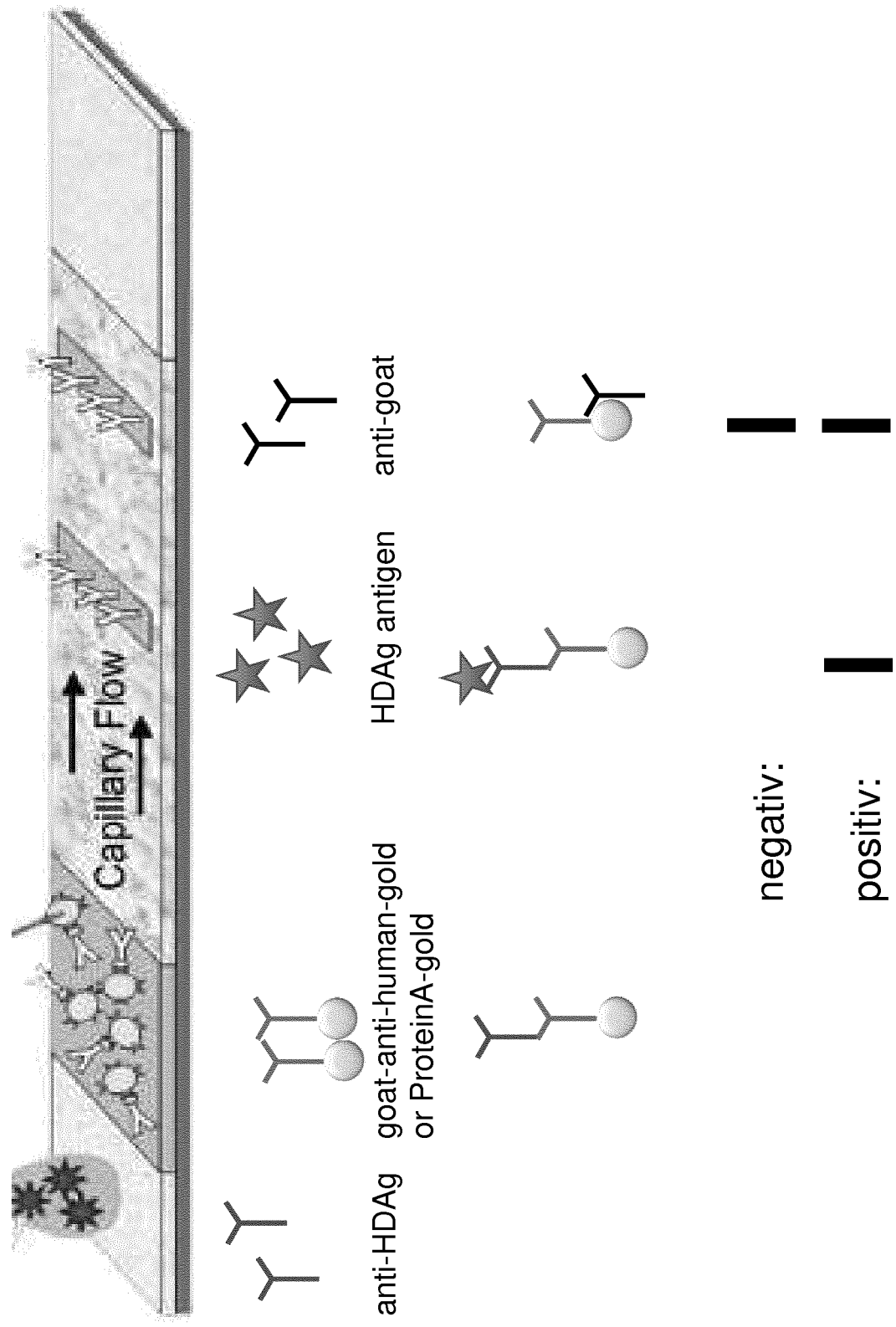

FIG. 4. Layout of the LFA of the Invention: A Direct LFA for HDAg-Abs.

A, A general layout of a LFA is shown. Note that the LFA outlined in the scheme detects an analyte by using antibodies, while the present invention detects antibodies against HDAg by immobilized antigen.

B, Patient serum containing anti-HDAg antibodies is placed on the sample pad (left). All human antibodies are labeled with anti-human-gold or ProteinA-gold on the conjugate pad. HDAg-specific antibodies bind to the recombinant HDAg on the test line and give a positive signal. Other non-HDAg-specific human antibodies migrate to the control line, where an antibody binds to the gold-labeled conjugate antibody and forms the control line to indicate that the test is valid.

Figure 5:
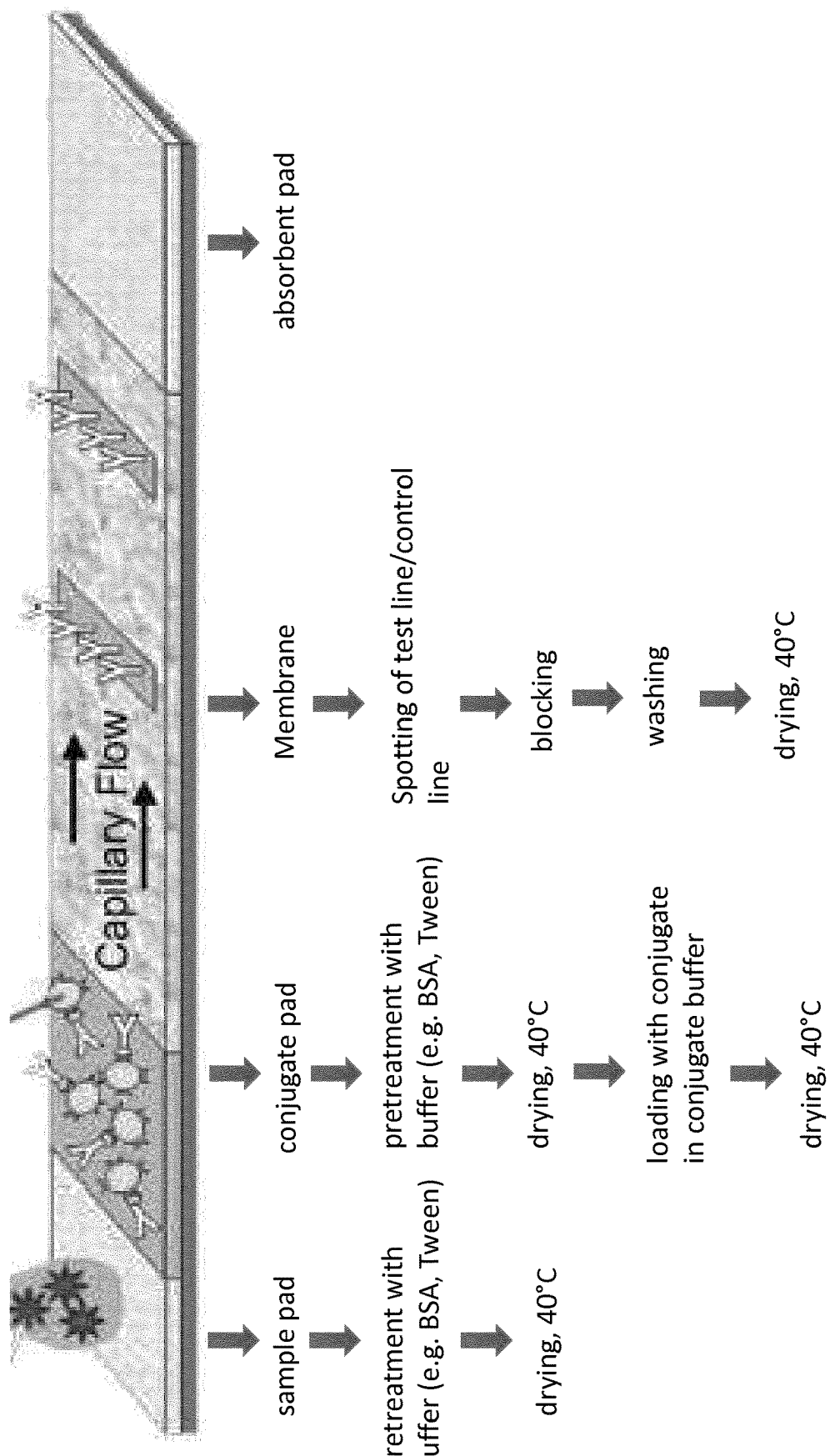

FIG. 5. Assembly of the LFA of the Invention.

Sample and conjugate pad are pretreated with buffer containing blocking agent (e.g. BSA) and surfactant (e.g. Tween-20). Pretreated conjugate pads are loaded with conjugate in buffer containing high sugar (e.g. 20% sucrose). Test and control lines are spotted on the membrane, which is subsequently blocked and dried. LFAs are assembled on a plastic backing card, cut into 0.4 cm strips and placed in a plastic housing.

Figure 6:
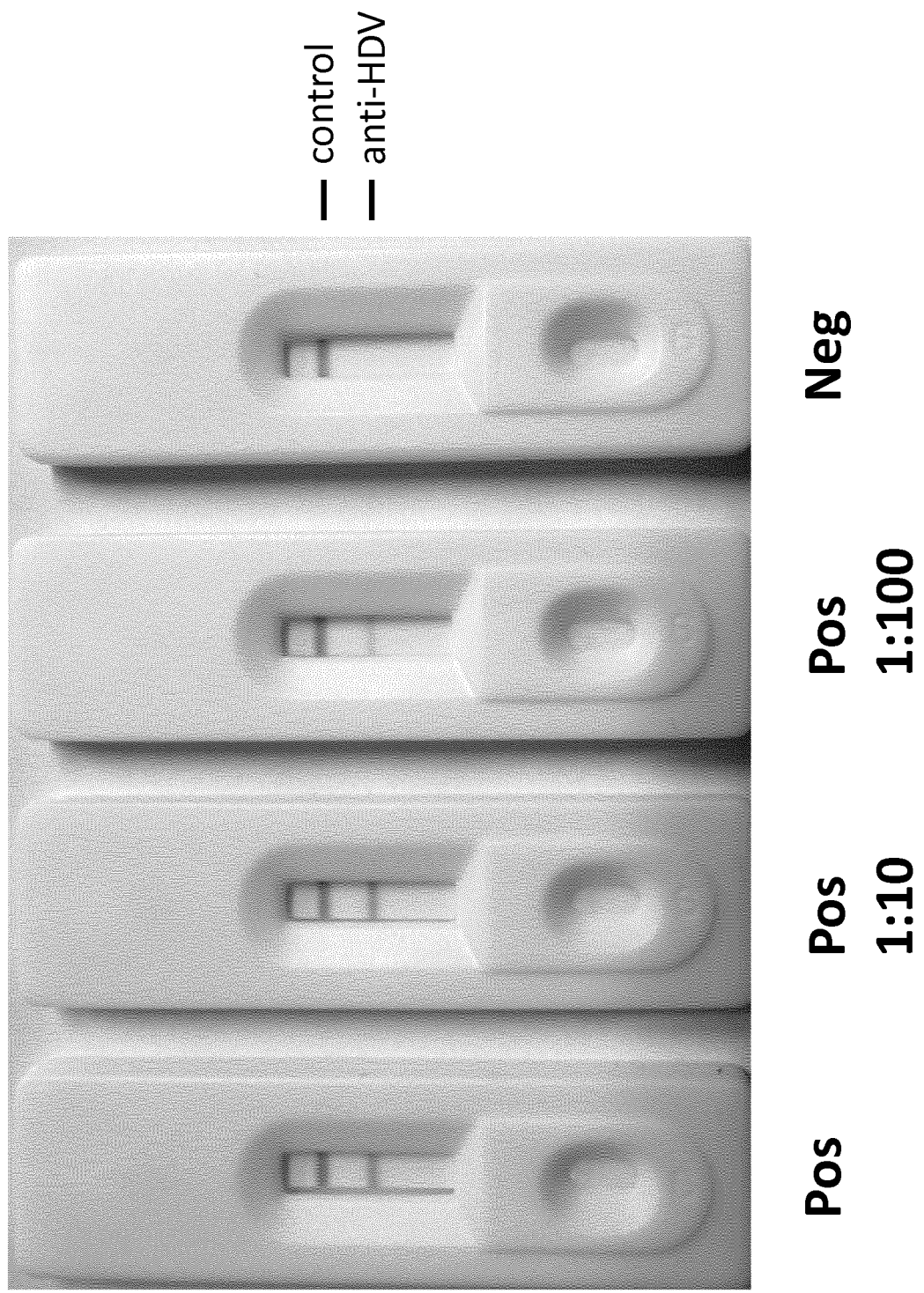

FIG. 6. Performance of the LFA of the Invention

The LFA was run with serum of an HBV/HDV co-infected patient (pos, left) or of a healthy patient (neg, right) or with different dilutions of the co-infected patient serum using the healthy patient serum as diluent (middle). Image was taken after 10 min of running time. The upper red line represents the control line, while the lower line represents the test line detecting anti-HDAg antibodies. Note that even in the 1:100 dilution a clear signal at the test line is visible, which is completely absent in the healthy patient serum.

Figure 7:
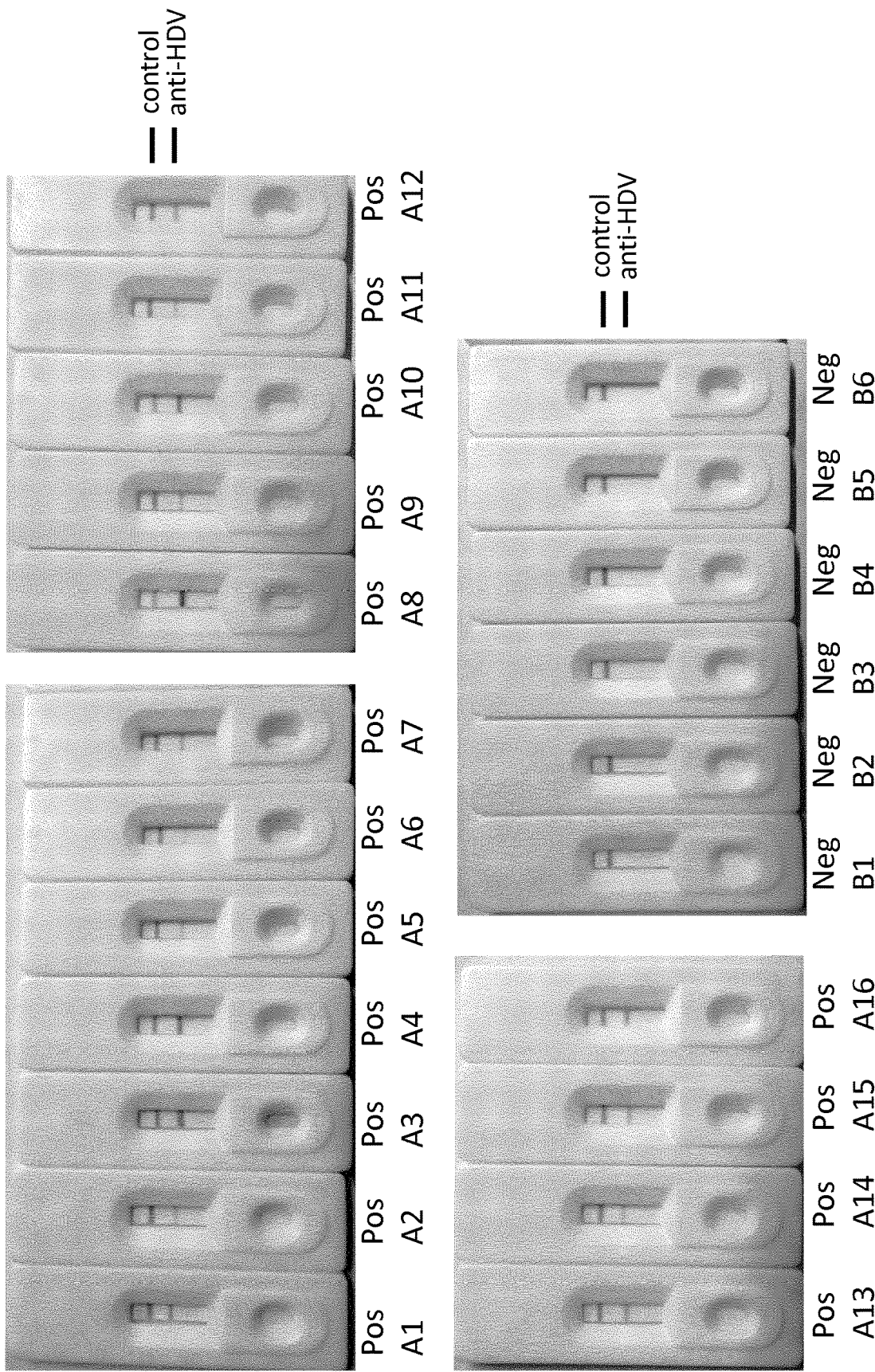

FIG. 7. Screening of 16 Infected and 6 Healthy Patients with the LFA of the Invention.

The LFA was run with serum of 16 HBV/HDV co-infected (PosA1-A16) and 6 healthy patients (Neg B1-B6). Image was taken after 10 min of running time.

Figure 8:
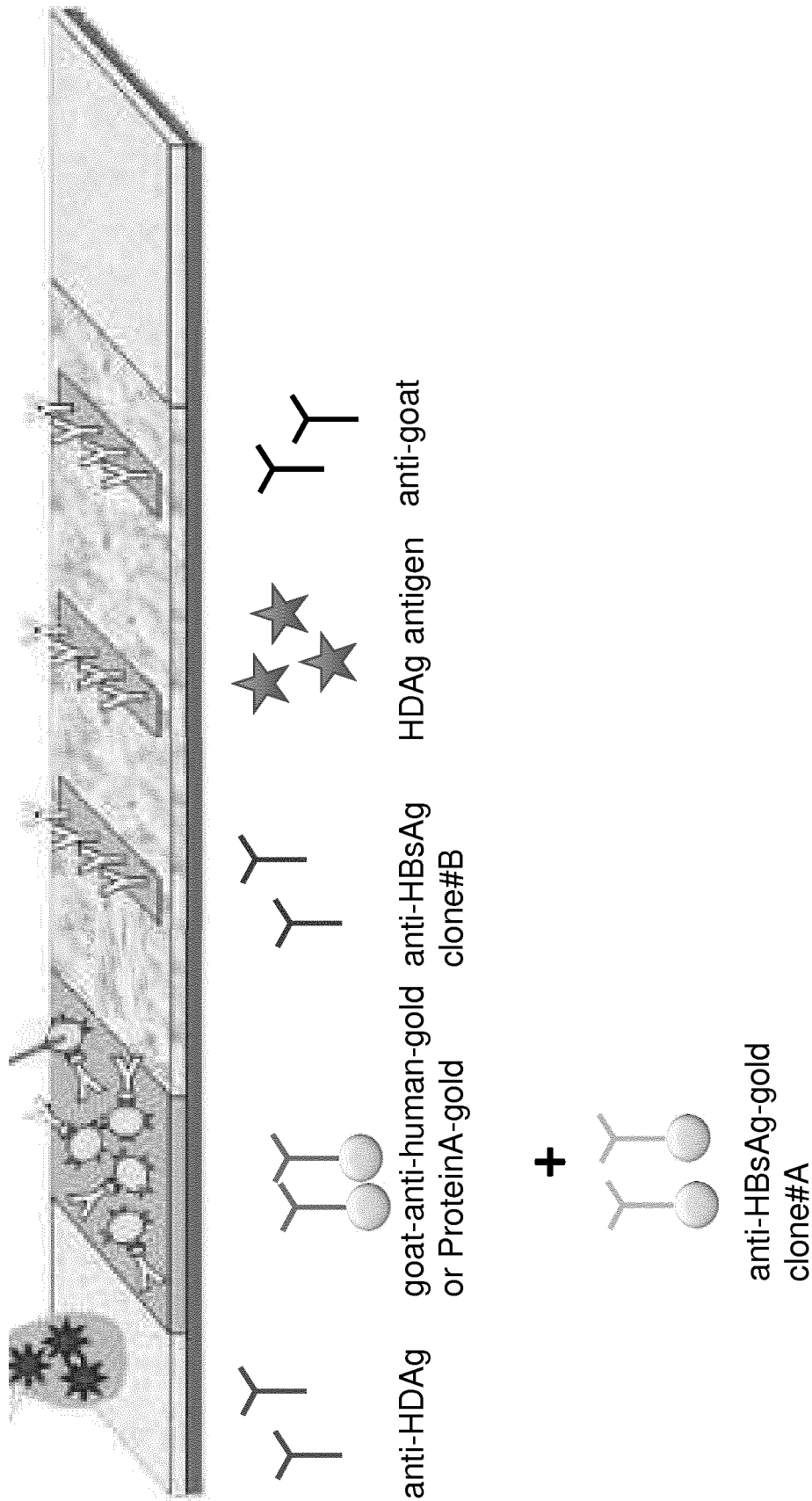

FIG. 8. Layout of a Multiplex LFA to Simultaneously Detect HBsAg and Anti-HDAg.

The Layout of the Multiplex LFA is similar to the single anti-HDAg LFA of this invention (FIG. 4B) with the addition of a second test line with immobilized anti-HBsAg antibodies and a second anti-HBsAg coupled to gold-nanoparticles on the conjugate pad (both anti-HBsAg antibodies are of different clones).

Figure 9:
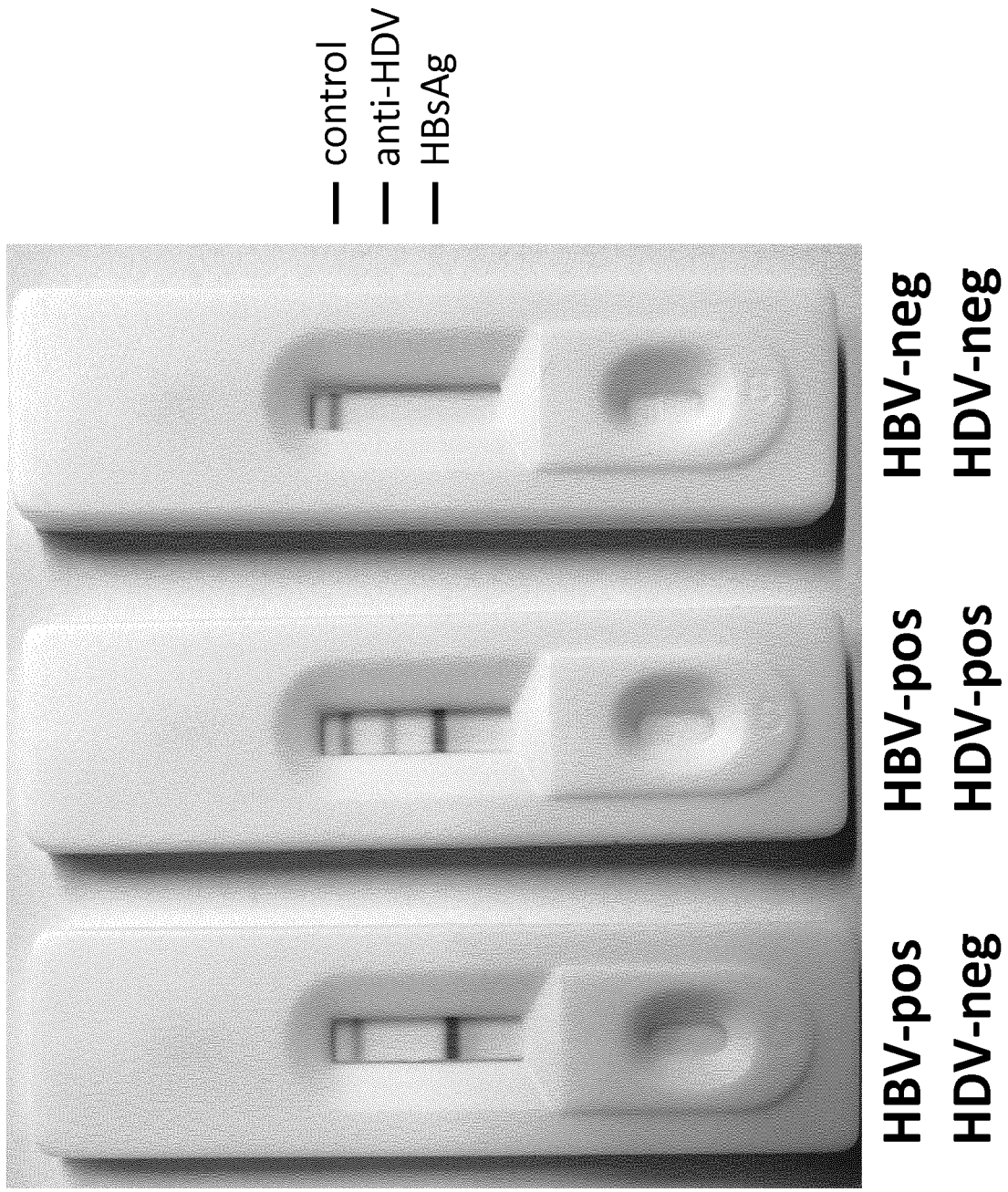

FIG. 9. Performance of a Multiplex LFA to Simultaneously Detect HBsAg and Anti-HDAg.

The Multiplex LFA was run with serum of an HBV mono-infected patient (left), an HBV/HDV co-infected patient (middle) or a healthy patient (right). Image taken after 10 min run time.

Figure 10:
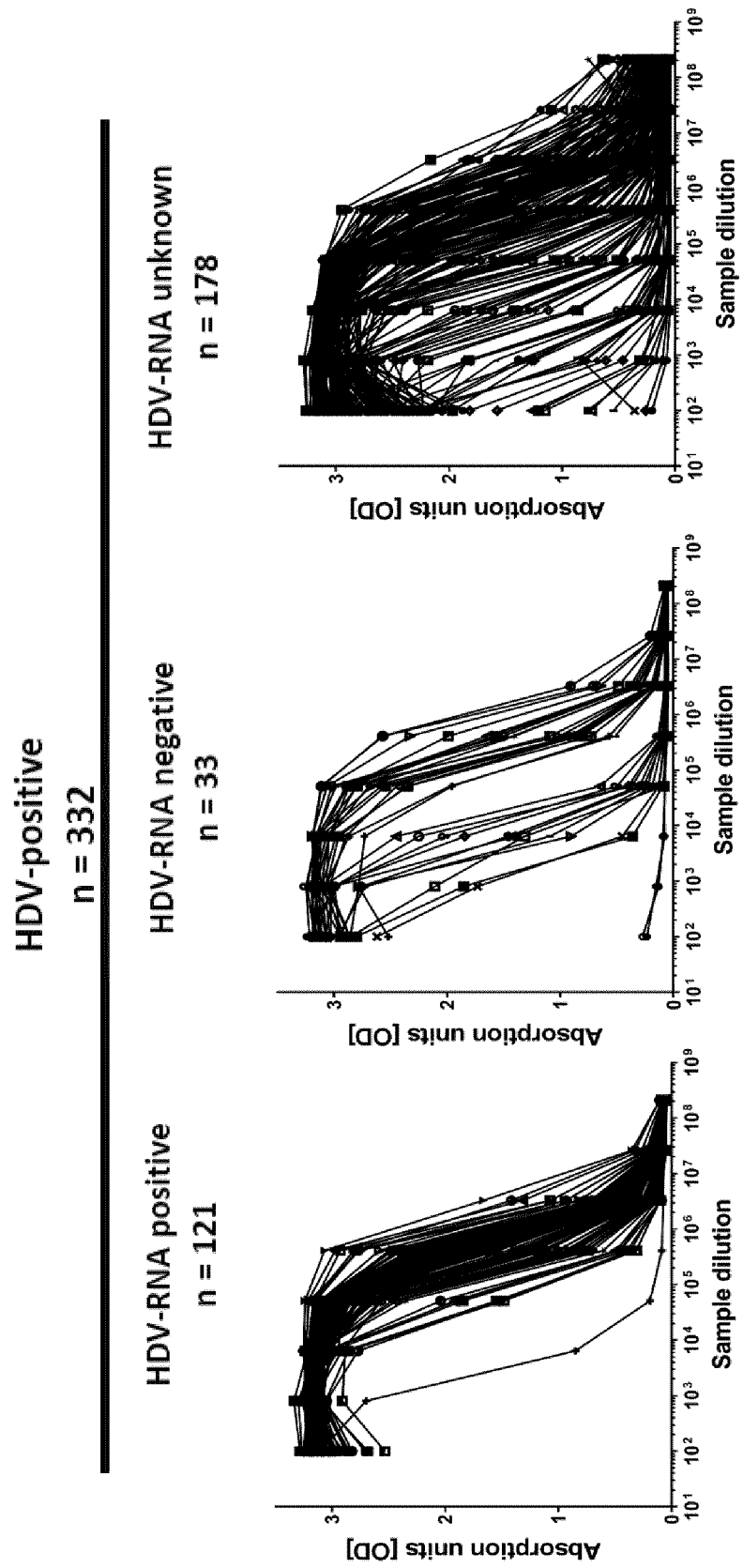
Figure 10:
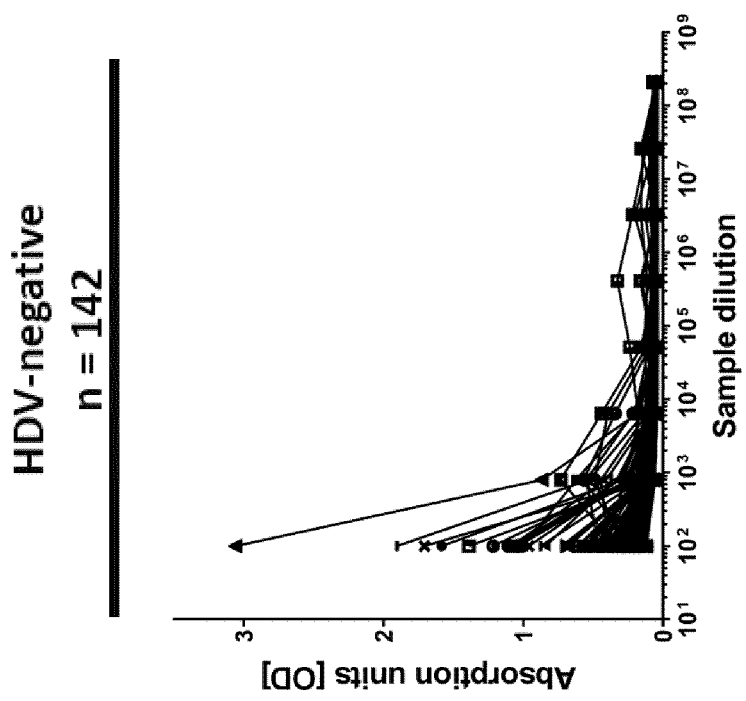

FIG. 10. Characterization of Validation Samples.

For assay validation, a collection of HDV-positive and HDV-negative samples was established. HDV positivity or negativity was determined with the DiaSorin anti-HD manual plate ELISA assay.

A and B, Analysis of all validation samples for quantitative levels of anti-HDV antibodies by direct plate ELISA with coated HDAg and increasing sample dilutions.

FIG. 11. Assay Validation.

All validation samples were applied to the LFA of the invention, i.e. the POC test.

A, Using the DiaSorin assay as gold standard, a high sensitivity of 94.6% for the POC test was calculated.

B, to D, The quantitative anti-HDV data were plotted with the POC test results.

Figure 12:
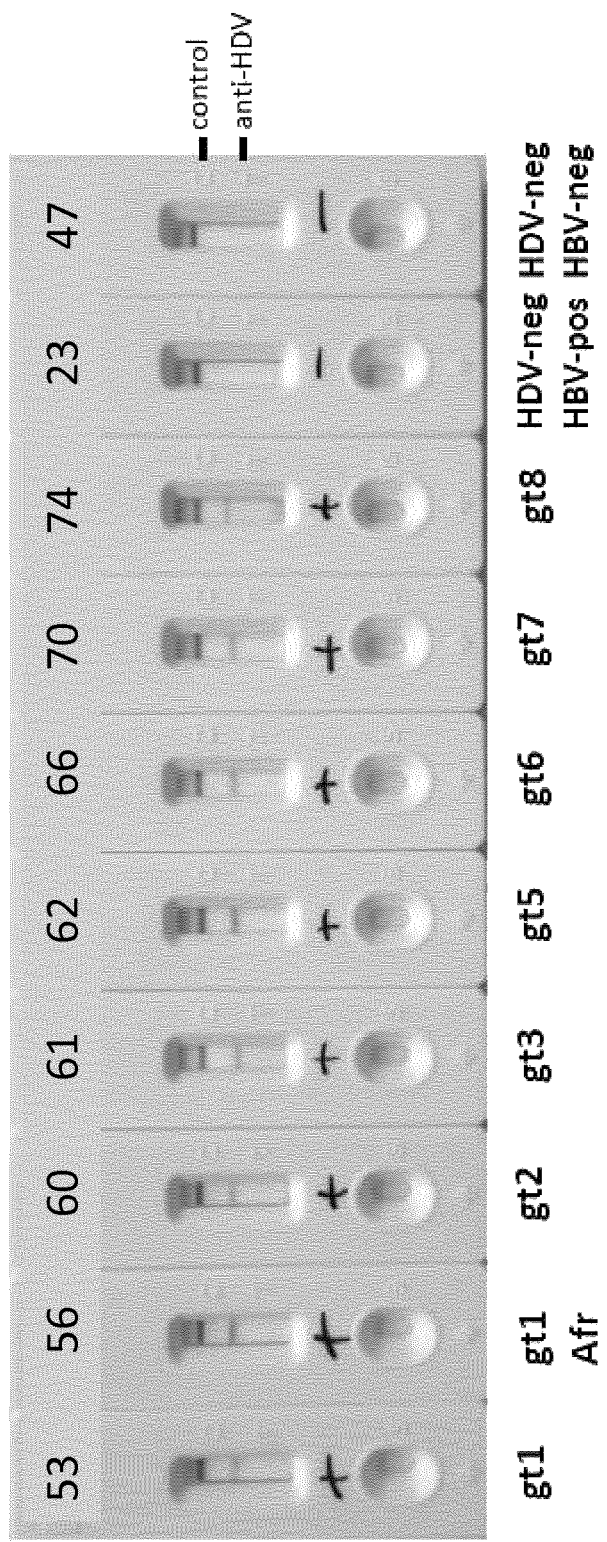

FIG. 12. Analysis of Sera with Different HDV Serotypes.

The LFA (i.e. POC test) was performed with sera of patients infected with different genotypes (gt) of HDV to validate the pan-genotypic specificity of the assay. Antibodies of all tested genotypes can be detected in the LFA (i.e. POC test).

EXAMPLES

Example 1 Materials and Methods 1.1 Protein Expression and Purification

The open reading frame of L-HDAg-consensus-His was cloned into the bacterial expression vector pET, transformed into *E. coli* BL21 and protein expression was induced by addition of 1 mM IPTG for 3 h at 37° C. Bacteria were lysed using a microfluidizer, recombinant protein was solubilized in 8M Urea and purified using a nickel-sepharose column (HisTrap, GE Healthcare) on an Äkta HPLC system. Elution was performed using a linear imidazole gradient.

1.2 ELISA

Recombinant protein was coated on a 96-well ELISA plate (Greiner Bio-One) at 2 µg/ml and blocked with 3% BSA/PBS/0.05% Tween-20. Human serum samples were diluted in 0.1% BSA/PBS/0.05% Tween-20 buffer at the indicated dilutions and incubated on the plates for 1 h at 37° C. After washing, the plates were incubated with a secondary goat-anti-human-perodxidase antibody (Jackson Immuno, 1:5000 dilution). After washing, the enzymatic reaction was started by incubation with TMB substrate (eBioscience) for 5 min at RT and stopped by addition of 1M phosphoric acid. Absorption at 450 nm was measured using a 96-well plate reader (Tecan).

1.3 Assembly of Lateral Flow Assay

Lateral flow assays were assembled exclusively with material of the LFA material starter kit (DCN Diagnostics). Recombinant L-HDAg-consensus-His at the test line and donkey-anti-goat (Novo Nordisk) at the control line were applied at 2 mg/ml using the applicator AS30 (biostep) with 1 µl/cm volume. Membrane was subsequently blocked with 2% BSA, washed with PBS/0.05% Tween-20 and dried. Sample and conjugate pads were pretreated with sample pad buffer and goat-anti-human-Gold (BioAssayWorks) was applied to the conjugate pad in a buffer containing 20% sucrose and 5% trehalose. After drying of the individual parts, the LFA was assembled on a plastic backing card, cut into 4 mm strips and placed into plastic cassette housings.

1.4 DiaSorin Assay

The manual plate ELISA for anti-HDAg detection "ETI-AB-DELTAK-2 anti-HDV" (Diasorin, Italy, order no P2808) was used according to the manufacturer's instructions.

1.5 HDV Samples and Patient Sera/Collection of Serum Samples from all Genotypes Serum/plasma samples of HDV-infected patients were provided by the University Hospital Heidelberg, Hannover Medical School, Ankara Medical School, French blood bank (EFS) and the company Biomex (Heidelberg, Germany). All negative samples were purchased from Biomex (Heidelberg, Germany). Serum samples of patients infected with different HDV genotypes were characterized and provided by the Laboratoire de Microbiologie Clinique, Hôpital Avicenne (APHP, Bobigny, France). All serum/plasma samples were stored at −80° C. until use.

Example 2

2.1 Characterization of Validation Samples.

For assay validation, a collection of HDV-positive and HDV-negative samples was established from routine clinical diagnostics, from HDV clinical studies or commercial vendors. See Table 1 below. HDV positivity or negativity was determined with the DiaSorin anti-HD manual plate ELISA assay.

TABLE 1

Characteristics of validation samples

| | | HDV-positive n = 332 | HDV-negative n = 142 |
|---|---|---|---|
| HBsAg status | HBsAg-positive | 332 | 62 |
| | HBsAg-negative | 0 | 80 |
| HDV-RNA status | RNA-positive | 121 | 0 |
| | RNA-negative | 33 | 0 |
| | RNA-unknown | 178 | 142 |
| Sample matrix | Serum | 299 | 42 |
| | EDTA-Plasma | 21 | 30 |
| | Citrate-Plasma | 12 | 70 |

To obtain quantitative levels of anti-HDV antibodies in the validation samples, a quantitative ELISA assay was established: ELISA plates were coated with recombinant HDAg, incubated with different dilutions of the samples and bound antibodies were detected using a peroxidase-labeled antibody, as described above. See FIG. 10A and B.

2.2 Assay Validation

All validation samples were applied to the LFA of the invention, i.e. the POC test.

Using the DiaSorin assay as gold standard, a high sensitivity of 94.6% for the POC test was calculated, see FIG. 11A.

When plotting the quantitative anti-HDV data with the POC test results, it is apparent that all RNA-positive HDV sera can be detected with the POC (see FIG. 11C) and only samples with very low to undetectable levels of anti-HDV are negative in in the POC test (see FIG. 11D).

Example 3

Analysis of Sera with Different HDV Genotypes

The POC test was performed with sera of patients infected with different genotypes (gt) of HDV to validate the pan-genotypic specificity of the assay. As can be seen in FIG. 12, antibodies of all tested genotypes 1 to 8 can be detected in the POC test.

Example 4

Multiplex LFA for Simultaneous Detection of HBsAg and Anti-HDV

Rapid POC assays for HBsAg to diagnose an HBV infection are already marketed. In a proof-of-concept study, the anti-HDV assay of the invention was combined with an HBsAg assay on a multiplex LFA strip, as shown in FIG. 8.

The multiplex strips were assayed with sera of HBV/HDV co-infected, HBV-monoinfected or healthy patients. As can be seen in FIG. 9, the LFA/POC test can be multiplexed to simultaneously detect HBsAg and anti-HDV.

The features disclosed in the foregoing description, in the claims and/or in the accompanying drawings may, both separately and in any combination thereof, be material for realizing the invention in diverse forms thereof.

REFERENCES

Bazinet M., Pantea V., Cebotarescu V., Cojuhari L., Jimbei P., Vaillant A. Hdv2 o-09: Rep 2139 monotherapy and combination therapy with pegylated interferon: Safety and potent reduction of HBsAg and HDV RNA in caucasian patients with chronic HBV/HDV co-infection. J. Viral Hepat. 2015; 22:5-6.

Bazinet M., Pantea V., Cebotarescu V., Cojuhari L., Jimbei P., Albrecht J., Schmid P., Karimzadeh H., Roggendorf M., Vaillant A. Update on the safety and efficacy of rep 2139 mono-therapy and subsequent combination therapy with pegylated interferon α-2a in chronic HBV/HDV co-infection in caucasian patients. Hepatology. 2015; 62:222A.

Blank A, Markert C, Hohmann N, Carls A, Mikus G, Lehr T, Alexandrov A, Haag M, Schwab M, Urban S, Haefeli W E. First-in-human application of the novel hepatitis B and hepatitis D virus entry inhibitor myrcludex B. J Hepatol. 2016 September; 65(3):483-9.

Bogomolov P, Alexandrov A, Voronkova N, Macievich M, Kokina K, Petrachenkova M, Lehr T, Lempp F A, Wedemeyer H, Haag M, Schwab M, Haefeli W E, Blank A, Urban S. Treatment of chronic hepatitis D with the entry inhibitor myrcludex B: First results of a phase Ib/IIa study. J Hepatol. 2016 September; 65(3):490-8.

Koh C., Yurdaydin C., Cooper S. L., Cory D., Dahari H., Haynes-Williams V., Winters M., Bys M., Choong I., Idilman R., et al. Prenylation inhibition with lonafarnib decreases hepatitis D levels in humans. Hepatology. 2014; 60:1092A.

Koh C., Canini L., Dahari H., Zhao X., Uprichard S. L., Haynes-Williams V., Winters M. A., Subramanya G., Cooper S. L., Pinto P., et al. Oral prenylation inhibition with lonafarnib in chronic hepatitis D infection: A proof-of-concept randomised, double-blind, placebo-controlled phase 2a trial. Lancet. Infect. Dis. 2015; 15:1167-1174. doi: 10.1016/S1473-3099(15)00074-2.

Lempp F A, Urban S. Hepatitis Delta Virus: Replication Strategy and Upcoming Therapeutic Options for a Neglected Human Pathogen. Viruses. 2017; 9(7). pii: E172. doi: 10.3390/v9070172. Review.

Poutay D., Sabra M., Abou-Jaoude G., Chemin I., Trepo C., Vaillant A., Sureau C. P177: Nucleic acid polymers are efficient in blocking hepatitis delta virus entry in vitro. J. Viral Hepat. 2015; 22:107.

Urban S, Bartenschlager R, Kubitz R, Zoulim F. Strategies to inhibit entry of HBV and HDV into hepatocytes. Gastroenterology. 2014 July; 147(1):48-64.

Vaillant A. Nucleic acid polymers: Broad spectrum antiviral activity, antiviral mechanisms and optimization for the treatment of hepatitis B and hepatitis D infection. Antivir. Res. 2016; 133:32-40. doi: 10.1016/j.antiviral.2016.07.004.

Yuidaydin C., Idilman R., Choong L, Kalkan C., Keskin O., Karakaya M. F., Tuzun A. E., Karatayli E., Bozdayi M., Cory D., et al. 0118: Optimizing the prenylation inhibitor lonafarnib using ritonavir boosting in patients with chronic delta hepatitis. J. Hepatol. 2015; 62:S252. doi: 10.1016/S0168-8278(15)30137-9.

The invention claimed is:

1. A polypeptide comprising an amino acid sequence selected from
   an amino acid sequence of SEQ ID NO: 1 or SEQ ID NO: 2,
   an amino acid sequence comprising amino acid residues 1 to 195 of SEQ ID NOs: 1 or 2,
   an amino acid sequence comprising amino acid residues 60 to 214 of SEQ ID NOs: 1 or 2, and
   an amino acid sequence having at least 99% sequence identity to SEQ ID NO: 1.

2. A nucleic acid encoding a polypeptide of claim 1.

3. An in vitro method for detecting the presence of hepatitis D virus (HDV) and/or for diagnosing an HDV infection and/or for monitoring the treatment of an HDV infection in a sample of a subject, said method comprising;
   providing the polypeptide of claim 1; and
   detecting for IgG antibodies against the Hepatitis Delta Antigen (HDAg) in said sample.

4. The method of claim 3, wherein the sample is serum, plasma, whole blood or saliva,
   and/or wherein HDV and HDV infections of all genotypes can be detected,
   and/or wherein one or more further infections are detected.

5. An immunographic device for in vitro detecting the presence of Hepatitis D virus (HDV) in a sample of a subject, diagnosing an HDV infection and/or monitoring the treatment of an HDV infection, said device comprising a solid carrier coated with an anti-HDV IgG antibody binding agent,
   wherein the anti-HDV IgG antibody binding agent is the polypeptide of claim 1.

6. The immunographic device of claim 5, wherein the immunographic device comprises a porous membrane operably connected to
   (a) a sample portion/pad,
   (b) a conjugate portion/pad,
   (c) a test portion/line comprising said anti-HDV IgG antibody binding agent,
   (d) a control portion/line; and
   (e) an absorbent portion/pad.

7. The immunographic device of claim 5, wherein the immunographic device is a lateral flow assay (LFA) device.

8. The immunographic device of claim 5, wherein the sample is serum, plasma, whole blood or saliva,
   and/or wherein HDV and HDV infections of all genotypes can be detected,
   and/or wherein one or more further infections are detected.

9. The immunographic device of claim 6, wherein the conjugate portion/pad comprises a detection marker.

10. The immunographic device of claim 6, wherein the control portion/line comprises a binding agent to a detection marker or a moiety carrying the detection marker.

11. A kit for in vitro detecting the presence of Hepatitis D virus (HDV) in a sample of a subject, diagnosing an HDV infection and/or monitoring the treatment of an HDV infection, wherein the kit comprises:
  a) an immunographic device according to claim 9; and
  b) instructions for using the immunographic device to detect the presence of said anti-HDV IgG antibodies in the sample,
  and/or HDV and HDV infections of all genotypes can be detected,
  and/or further infections are detected, such as HBV infection.

12. The polypeptide of claim 1, consisting of an amino acid sequence selected from
  an amino acid sequence of SEQ ID NO: 1 or SEQ ID NO: 2,
  an amino acid sequence consisting of amino acid residues 1 to 195 of SEQ ID NOs: 1 or 2,
  an amino acid sequence consisting of amino acid residues 60 to 214 of SEQ ID NOs: 1 or 2, and
  an amino acid sequence having at least 99% sequence identity to SEQ ID NO: 1.

13. The method of claim 3, which is a point of care method.

14. The method of claim 4, wherein HBV is also detected.

15. The device of claim 7, which is a point of care device.

16. The device of claim 8, wherein HBV is also detected.

17. The device of claim 9, wherein the detection marker comprises a colloidal metal or latex beads.

18. The device of claim 9, wherein the detection marker is directly or indirectly bound to an antibody or an antibody-binding protein.

19. The device of claim 18, wherein the detection marker is directly or indirectly bound to an anti-human antibody, Protein A, or Protein G.

20. The kit of claim 11, wherein the sample is serum, plasma, whole blood or saliva.

* * * * *

SEQUENCE LISTING

```
<160> NUMBER OF SEQ ID NOS: 2

<210> SEQ ID NO 1
<211> LENGTH: 214
<212> TYPE: PRT
<213> ORGANISM: Artificial Sequence
<220> FEATURE:
<223> OTHER INFORMATION: Synthetic HDAg Sequence (Consensus)

<400> SEQUENCE: 1

Met Ser Arg Ser Glu Ser Lys Lys Asn Arg Gly Gly Arg Glu Glu Ile
1               5                   10                  15

Leu Glu Gln Trp Val Ser Gly Arg Lys Lys Leu Glu Asp Leu Glu Arg
            20                  25                  30

Asp Leu Arg Lys Val Lys Lys Lys Ile Lys Lys Leu Glu Asp Glu Asn
        35                  40                  45

Pro Trp Leu Gly Asn Ile Lys Gly Ile Leu Gly Lys Lys Asp Lys Asp
    50                  55                  60

Gly Glu Gly Ala Pro Pro Ala Lys Arg Ala Arg Thr Asp Gln Met Glu
65                  70                  75                  80

Val Asp Ser Gly Pro Arg Lys Arg Pro Leu Arg Gly Gly Phe Thr Asp
                85                  90                  95

Lys Glu Arg Gln Asp His Arg Arg Arg Lys Ala Leu Glu Asn Lys Lys
            100                 105                 110

Lys Gln Leu Ser Ala Gly Gly Lys Asn Leu Ser Lys Glu Glu Glu Glu
        115                 120                 125

Glu Leu Arg Arg Leu Thr Glu Glu Asp Glu Arg Arg Glu Arg Arg Val
    130                 135                 140

Ala Gly Pro Arg Val Gly Gly Val Asn Pro Leu Glu Gly Gly Pro Arg
145                 150                 155                 160

Gly Ala Pro Gly Gly Gly Phe Val Pro Ser Met Gln Gly Val Pro Glu
                165                 170                 175

Ser Pro Phe Thr Arg Thr Gly Glu Gly Leu Asp Ile Arg Gly Asn Gln
            180                 185                 190

Gly Phe Pro Trp Asp Ile Leu Phe Pro Ala Asp Pro Pro Phe Ser Pro
        195                 200                 205

Gln Ser Cys Arg Pro Gln
    210

<210> SEQ ID NO 2
<211> LENGTH: 222
<212> TYPE: PRT
<213> ORGANISM: Artificial Sequence
<220> FEATURE:
<223> OTHER INFORMATION: Synthetic HDAg Sequence (Consensus) with a His-
      tag for recombinant expression

<400> SEQUENCE: 2
```

```
Met Ser Arg Ser Glu Ser Lys Lys Asn Arg Gly Gly Arg Glu Glu Ile
1               5                   10                  15

Leu Glu Gln Trp Val Ser Gly Arg Lys Lys Leu Glu Asp Leu Glu Arg
                20                  25                  30

Asp Leu Arg Lys Val Lys Lys Lys Ile Lys Lys Leu Glu Asp Glu Asn
            35                  40                  45

Pro Trp Leu Gly Asn Ile Lys Gly Ile Leu Gly Lys Lys Asp Lys Asp
        50                  55                  60

Gly Glu Gly Ala Pro Pro Ala Lys Arg Ala Arg Thr Asp Gln Met Glu
65                  70                  75                  80

Val Asp Ser Gly Pro Arg Lys Arg Pro Leu Arg Gly Gly Phe Thr Asp
                85                  90                  95

Lys Glu Arg Gln Asp His Arg Arg Arg Lys Ala Leu Glu Asn Lys Lys
                100                 105                 110

Lys Gln Leu Ser Ala Gly Gly Lys Asn Leu Ser Lys Glu Glu Glu Glu
            115                 120                 125

Glu Leu Arg Arg Leu Thr Glu Glu Asp Glu Arg Arg Glu Arg Arg Val
    130                 135                 140

Ala Gly Pro Arg Val Gly Gly Val Asn Pro Leu Glu Gly Gly Pro Arg
145                 150                 155                 160

Gly Ala Pro Gly Gly Gly Phe Val Pro Ser Met Gln Gly Val Pro Glu
                165                 170                 175

Ser Pro Phe Thr Arg Thr Gly Glu Gly Leu Asp Ile Arg Gly Asn Gln
                180                 185                 190

Gly Phe Pro Trp Asp Ile Leu Phe Pro Ala Asp Pro Pro Phe Ser Pro
            195                 200                 205

Gln Ser Cys Arg Pro Gln His His His His His His His
210                 215                 220
```